United States Patent
Finke et al.

(10) Patent No.: US 9,901,651 B2
(45) Date of Patent: Feb. 27, 2018

(54) SYSTEM AND METHOD FOR TREATMENT OF A SURFACE OF AN INJECTION DEVICE

(71) Applicant: Covidien LP, Mansfield, MA (US)

(72) Inventors: Melvin Finke, DeLand, FL (US); David Selvitelli, Suffield, CT (US)

(73) Assignee: KPR U.S., LLC, Mansfield, MA (US)

( * ) Notice: Subject to any disclaimer, the term of this patent is extended or adjusted under 35 U.S.C. 154(b) by 351 days.

(21) Appl. No.: 14/069,433

(22) Filed: Nov. 1, 2013

(65) Prior Publication Data
US 2014/0119986 A1   May 1, 2014

Related U.S. Application Data

(60) Provisional application No. 61/721,213, filed on Nov. 1, 2012, provisional application No. 61/875,274, filed
(Continued)

(51) Int. Cl.
*A61L 2/10* (2006.01)
*A61M 5/28* (2006.01)
(Continued)

(52) U.S. Cl.
CPC ............ *A61L 2/10* (2013.01); *A61M 5/288* (2013.01); *A61L 2202/23* (2013.01);
(Continued)

(58) Field of Classification Search
CPC ... A61L 2/10; A61L 2/08; A61L 2/081; A61L 2/088
See application file for complete search history.

(56) References Cited

U.S. PATENT DOCUMENTS 3,571,939 A * 3/1971 Paul .................... A61L 2/10
219/400
4,309,388 A    1/1982 Tenney et al.
(Continued)

FOREIGN PATENT DOCUMENTS

| EP | 2457550 A1 | 5/2012 |
| FR | 2250676 A1 | 6/1975 |
| WO | 94/04415 A1 | 3/1994 |

OTHER PUBLICATIONS

International Search Report and Written Opinion, dated Jan. 8, 2014, cited in International Application No. PCT/US2013/067943, International Filing Date Nov. 1, 2013, 12 pages.
(Continued)

*Primary Examiner* — Donald R Spamer
(74) *Attorney, Agent, or Firm* — Jacob R. Lenzke

(57) ABSTRACT

The disclosed embodiment relates to a system and method for treating a non-sterile surface of at least a component of a medical device, such as, but not limited to, a cartridge for an injection device. The system for treating a non-sterile surface of a medical device includes a source of electromagnetic radiation and, in some embodiments, a source of laminar airflow. The source of electromagnetic radiation provides exposure and the source of laminar airflow provides laminar airflow to the surface for treatment of the medical device. The method for treating a non-sterile surface includes exposing the non-sterile surface of a cartridge to a pulsed electromagnetic wave. In some embodiments, simultaneous to the pulsed electromagnetic radiation exposure, a laminar airflow can be directed perpendicular to the surface of the cartridge.

23 Claims, 15 Drawing Sheets

Related U.S. Application Data on Sep. 9, 2013, provisional application No. 61/875,270, filed on Sep. 9, 2013.

(51) Int. Cl.
*A61M 5/00* (2006.01)
*A61M 5/31* (2006.01)

(52) U.S. Cl.
CPC ..... *A61M 5/001* (2013.01); *A61M 2005/3139* (2013.01); *A61M 2207/00* (2013.01)

(56) References Cited

U.S. PATENT DOCUMENTS

| | | | |
|---|---|---|---|
| 4,860,643 A * | 8/1989 | Spearow | B08B 15/023 126/299 R |
| 4,910,942 A | 3/1990 | Dunn et al. | |
| 5,431,201 A | 7/1995 | Torchia et al. | |
| 2004/0241041 A1 * | 12/2004 | Woodworth | A61J 1/1406 422/22 |
| 2006/0151714 A1 | 7/2006 | Thilly et al. | |
| 2006/0225809 A1 * | 10/2006 | Py | B65B 3/022 141/93 |
| 2007/0258851 A1 | 11/2007 | Fogg et al. | |
| 2008/0181826 A1 | 7/2008 | Windsheimer | |
| 2008/0199353 A1 * | 8/2008 | Mlodzinski | A61J 1/20 422/24 |
| 2010/0005760 A1 | 1/2010 | Matheyka | |
| 2012/0141322 A1 | 6/2012 | Fogg | |
| 2012/0141323 A1 | 6/2012 | Fogg | |

OTHER PUBLICATIONS

European Search Report dated Apr. 25, 2012, cited in EP Publication No. EP 2 457 550, Publication Date of May 30, 2012, 3 pages.
International Preliminary Report on Patentability, dated Feb. 11, 2015, issued in International Application No. PCT/US/2013/067943, 6 pages.
Communication pursuant to Rules 161(1) and 162 EPC issued in EP Application No. EP 13792544.2, dated Jun. 10, 2015, 2 pages.
Office Action dated Apr. 4, 2017 in related European Application No. 13792544.2, 8 pages.

* cited by examiner

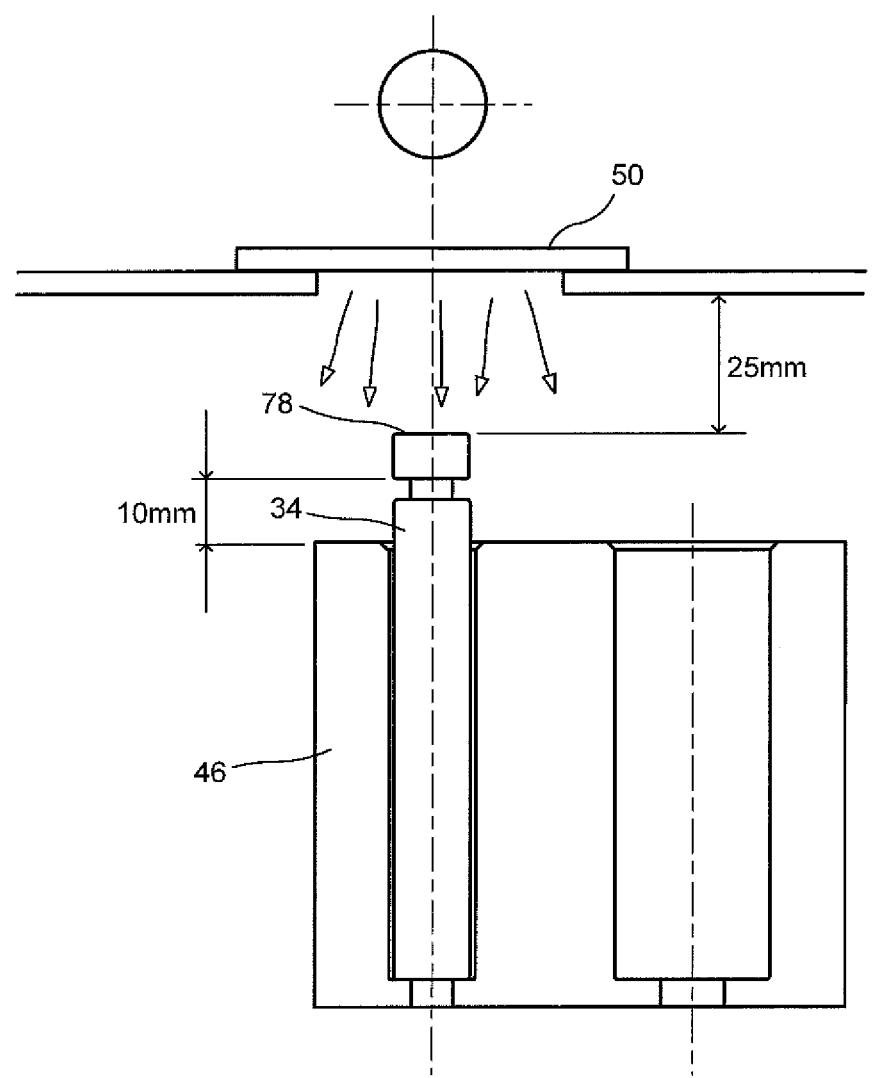
F I G. 1B

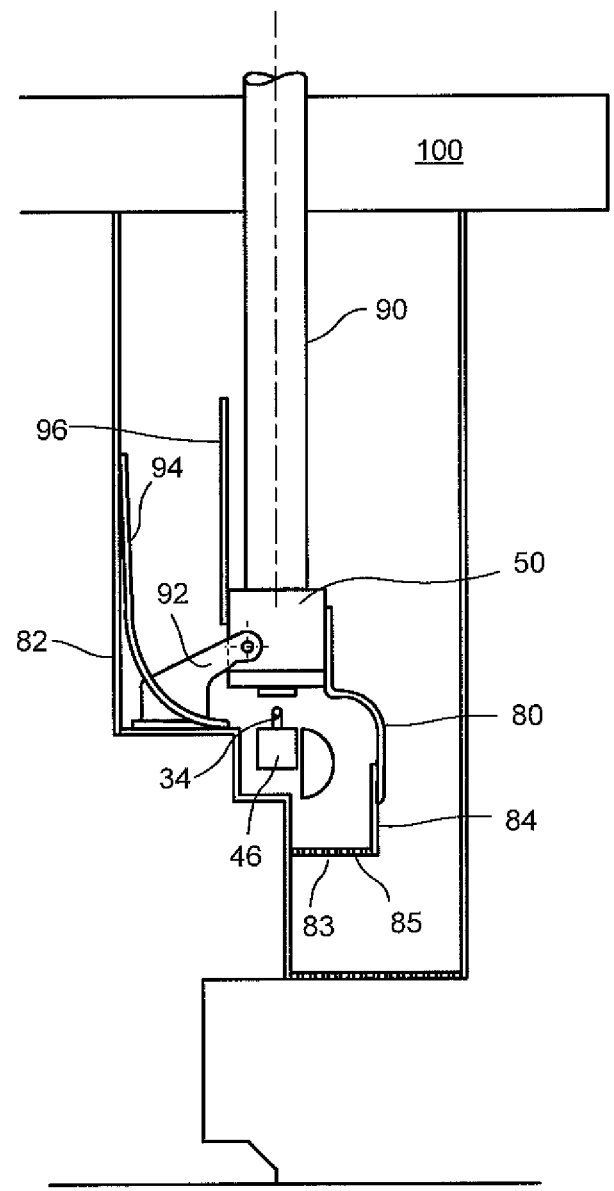
F I G. 4

```
     ┌─────────────┐  ╱─ 1000
     │   Begin     │
     └─────────────┘
            │
            ▼
┌──────────────────────────────┐
│ Expose the non-sterile surface to │ ── 1004
│   an electromagnetic wave    │
└──────────────────────────────┘
            │
            ▼
┌──────────────────────────────┐
│ Direct an ISO class 5 laminar airflow │ ── 1008
│ perpendicular to the surface of the   │
│      electromagnetic wave             │
└──────────────────────────────┘
            │
            ▼
┌──────────────────────────────┐
│ Assembly a sterilized needle assembly and │ ── 1010
│ the cartridge under ISO class 5 laminar   │
│              airflow                      │
└──────────────────────────────┘
            │
            ▼
     ┌─────────────┐  ╱─ 1012
     │ End process │
     └─────────────┘
```

F I G. 8B

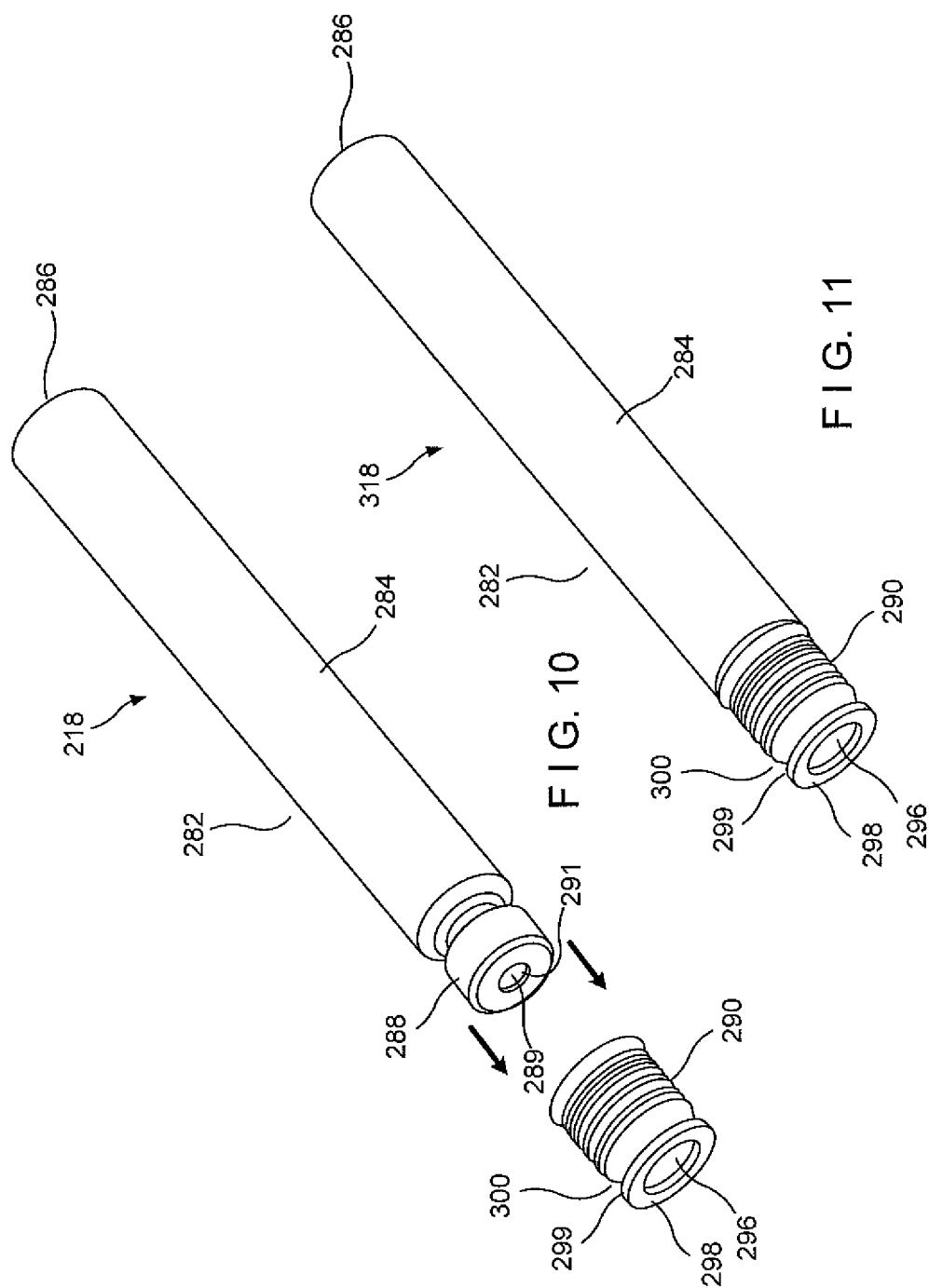

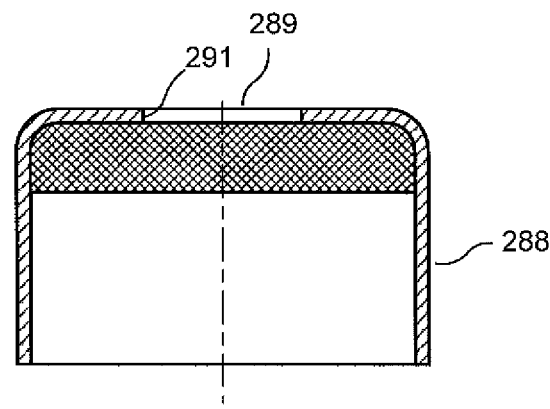
F I G. 12A
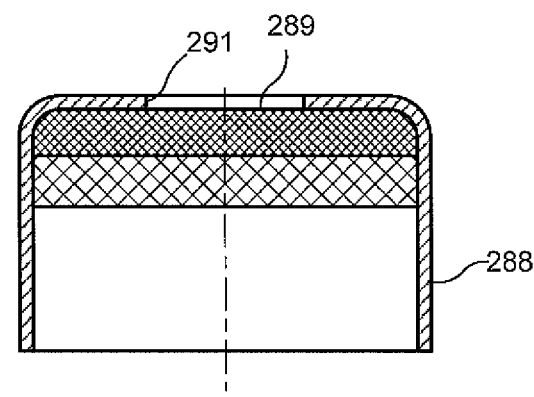
F I G. 12B

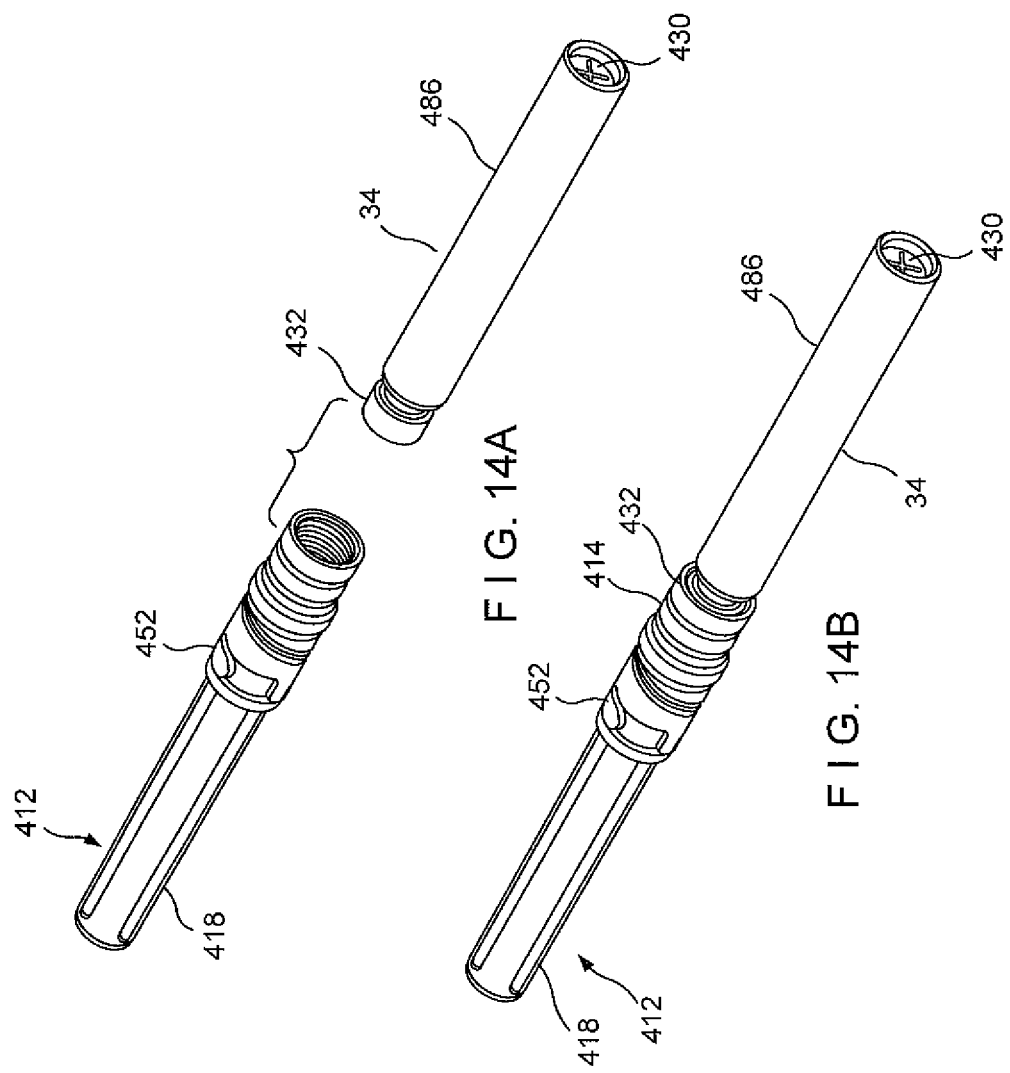

SYSTEM AND METHOD FOR TREATMENT OF A SURFACE OF AN INJECTION DEVICE

RELATED APPLICATIONS

This application claims priority under 35 U.S.C. § 119(e) to U.S. Provisional Patent Application Ser. No. 61/721,213, entitled "Cartridge Surface Sterilization," filed on Nov. 1, 2012, U.S. Provisional Patent Application Ser. No. 61/875,274 entitled "Sealed Self-Activating Injection Device for Delivery of Medicine from a Prefilled Cartridge or Vial" filed on Sep. 9, 2013, and U.S. Provisional Patent Application Ser. No. 61/875,270, entitled "Single-Use Device for Injection of Cartridge Drugs" filed on Sep. 9, 2013. The disclosures of all of these applications are hereby incorporated by reference in their entirety.

FIELD OF DISCLOSURE

Exemplary embodiments of the present disclosure pertain to a method and system for automated logarithmic reduction of contamination of a surface of a medical device or component thereof. In particular, this disclosure pertains to the use of pulsed electromagnetic radiation to result in a logarithmic reduction of contamination of a surface.

BACKGROUND

Conventionally, reusable injection devices for injectable agents need to go through repeated sterilizations. Alternatively, for example, selected components, such as the needle, need to be disposed of and replaced for each subsequent use. Pre-filled single-use injection devices are advantageous in that they eliminate the need for the medical practitioner to sterilize and re-fill the injection device. However, the manufacture of a pre-filled single-use injection device requires that sterility be established during the automated manufacture and assembly processes to assure that there is no contamination of the fluid pathway of the injection device.

SUMMARY

Exemplary embodiments of the present disclosure are related to treating a non-sterile surface of an object, for example, a medical device, with a source of electromagnetic radiation to result in a logarithmic reduction of contamination on the treated surface. A source of laminar airflow may be applied to the surface before, during or after treatment. The disclosed contamination reduction systems and methods are well suited for treatment of a non-sterile surface to allow formation of a fluid pathway free of accidental contamination during the assembly of the injection device.

Some embodiments are directed to a system of treating a non-sterile surface of a medical device. The medical device can have a surface exposed to a source of electromagnetic radiation. The system can further include a source of laminar airflow providing the surface for treatment with a laminar airflow.

Some embodiments are directed to a method for treating a non-sterile surface of an object. A medical device, or a component of a medical device, for example, a cartridge, can have a non-sterile surface that can be exposed to a pulsed electromagnetic wave. An ISO class 5 laminar airflow can be directed perpendicularly to the surface exposed to the pulsed electromagnetic wave. The sterilized needle assembly and the cartridge can be assembled under the ISO class 5 laminar airflow following treatment of the non-sterile surface.

Some embodiments are directed to a system that includes a source of pulsed electromagnetic radiation and a source of laminar airflow. The system can further include a fixture for receiving a medical device or a component thereof. The system can further include a conveyor for transporting the fixture.

The systems and methods taught herein allow an object with a contaminated outer surface, for example, a prefilled cartridge, to be brought into a clean room environment and treated in the clean room environment to decontaminate one or more outer surfaces. The object, for example, the prefilled cartridge, once treated can be assembled in the clean room environment with another object, for example, a needle assembly, to form in some embodiments a continuous sterile pathway from the cartridge to the tip of a needle cannula.

Any combination or permutation of embodiments is envisioned. Other objects and features are apparent from the following detailed description considered in conjunction with the accompanying drawings, wherein like reference numerals identify like elements. It is to be understood, however, that the drawings are designed as an illustration only and not as a definition of the limits of the present disclosure.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component can be labeled in every drawing. In the drawings:

FIG. 1B depicts a side cross-sectional view of an exemplary source of electromagnetic radiation and a medical device under treatment;

FIG. 4 depicts a cross-sectional view of an exemplary source of electromagnetic radiation and a shield that can be used in the system for treating non-sterilized surfaces;

FIG. 8B is a flow diagram that illustrates a second method of treating a non-sterilized surface in accordance with exemplary embodiments of the present disclosure;

FIG. 10 is a perspective partially exploded view illustrating the attachment of the cartridge-to-housing interface to the cartridge of the present disclosure;

FIG. 11 is a perspective view of the assembly of the cartridge-to-housing interface and the cartridge of the present disclosure;

FIGS. 12A and 12B are cross-sectional views of the cap and septum of the present disclosure;

FIG. 14A is a perspective, partially exploded view, illustrating the pre-armed cartridge assembly of the present disclosure; and FIG. 14B is a perspective view illustrated the pre-armed cartridge assembly of the present disclosure.

DETAILED DESCRIPTION

While the disclosed exemplary embodiments pertain to the treatment of a non-sterile surface of an object by electromagnetic radiation to result in a logarithmic reduction of contamination on the treated surface, for example, a cartridge and needle assembly for a pre-filled injection device, it should be understood that the disclosure is not so limited, and that the systems and methods of the present disclosure may be used to treat one or more surfaces of various devices, including, but not limited to, a broad range of medical devices.

Exemplary embodiments of the present disclosure are directed to systems and methods for treating one or more non-sterile surfaces of a medical device or a component thereof with a source of electromagnetic radiation to result in a logarithmic reduction of contamination on the treated surface. A source of laminar airflow may be applied to the surface before, during or after treatment.

In some embodiments, a cartridge holding an injectable agent and having a surface treated as taught herein can be assembled with a sterilized needle assembly under an ISO class 5 laminar airflow. As taught herein, exposing a surface to pulsed electromagnetic radiation can logarithmically reduce the contamination or bio burden on the surface exposed to the treatment.

As used herein, the term "injectable agent" refers to, but is not limited to, local anesthetics, therapeutic or pharmaceutical agents, cosmetic agents or other liquids, gels or powders in the medical, dental, veterinary or cosmetic fields.

Figure 1A:
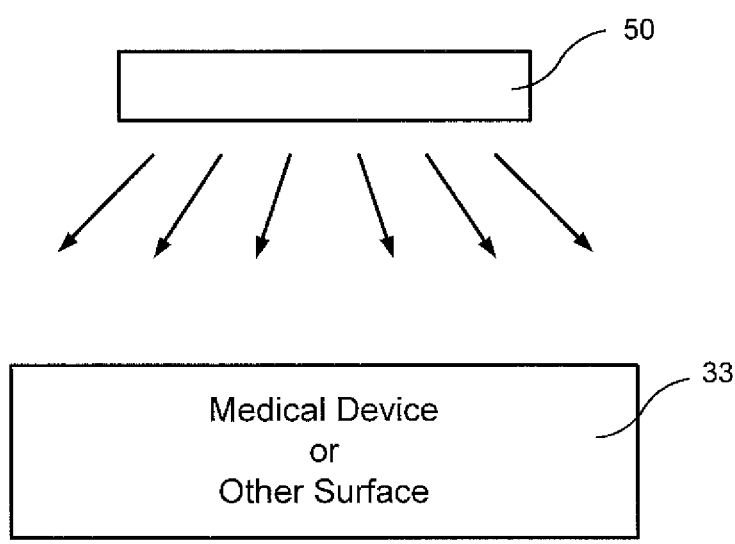
FIG. 1A depicts a side cross-sectional view of an exemplary source of electromagnetic radiation over a medical device under treatment.

Referring now to the drawings in detail wherein like numerals indicate like elements throughout the several views, one sees that FIG. 1A illustrates the general concept of irradiating a medical device 33, or component or surface thereof, or another device, component or surface, with electromagnetic radiation from electromagnetic radiation source 50. FIG. 1B depicts a side cross-sectional view of an exemplary source of electromagnetic radiation that can be used in the system for treating one or more non-sterilized surfaces of a medical device or a component thereof. As shown in FIG. 1B, a cartridge 34 (or other non-sterilized surface) can be disposed within a fixture 46. The cartridge 34 holds an injectable agent and can be placed in the fixture 46 in a vertical upright position. The surface to be treated can extend from the fixture 46. The fixture 46 can surround the cartridge 34 to prevent the electromagnetic radiation from entering the cartridge 34 and reduce exposure of the injectable agent to electromagnetic radiation as it is held within the fixture 46. In the present embodiment, the cartridge 34 can be inserted into the fixture 46 having 10 mm of the cartridge 34 exposed above the top surface of the fixture and the remainder of the cartridge encircled by the fixture. For example, the pulses can have a power density in the range for 0.01 to 50 J/cm$^2$ at the surface for treatment. The electromagnetic wave length can have a distribution with at least 70% of the electromagnetic energy is within the range of 170 nm to 2600 nm.

An electromagnetic radiation source 50 can be placed in a horizontal plane parallel to a surface 78 for treatment. The electromagnetic radiation source 50 surface can be spaced within a range of 20 to 30 mm, with 25 mm being used in many embodiments as the distance between the surface 78 for treatment and the electromagnetic radiation source so that electromagnetic radiation can be directed toward the surface 78 as it is transported past the electromagnetic radiation source 78. For example, the electromagnetic radiation source can treat the surface to reduce contamination to an acceptable level. For example, an acceptable level may be a Sterility Assurance Level (SAL) of ten to the minus four, ten to the minus five or ten to the minus six.

Figure 2:
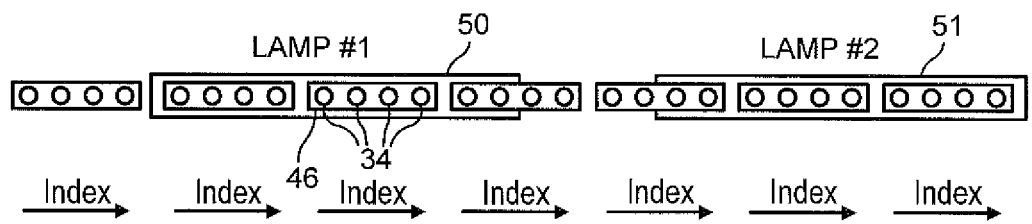
FIG. 2 depicts an overhead view of an exemplary source of electromagnetic radiation that can be used in the system for treating non-sterilized surfaces.

FIG. 2 depicts an overhead view of an exemplary source of electromagnetic radiation that can be used in the system for treating one or more non-sterilized surfaces. As shown in FIG. 2, the system can include a plurality of sources, first and second electromagnetic radiation sources 50, 51 can be arranged in a horizontal plane parallel to the fixture 46. The fixture 46 can contain the cartridges 34 and can pass under the electromagnetic radiation sources 50, 51. The fixtures 46 can be mobile, or in some embodiments, can remain stationary. In an exemplary embodiment, each fixture 46 can contain four cartridges 34. In some embodiments, the fixture 46 can hold more or less cartridges. In some embodiments, each process cycle can treat two and one half fixtures or ten cartridges. For example, the fixture 46 could hold anywhere from one to ten cartridges. One skilled in the art will realize depending on the device the fixture size will vary. Alternately, lamp size or configuration will also determine the size of the fixture. The electromagnetic radiation can be delivered in pulsed increments. In an exemplary embodiment, each cartridge can be flashed with twenty-five pulses of electromagnetic radiation. For example, the flashing frequency can be 0.32 seconds having five flashes per 1.6 seconds with incremental breaks of 0.4 seconds. The index time of the machine can be therefore configured to be two seconds and can have a stopping time for each index at 1.6 seconds. In some embodiments, each cartridge can stop under an electromagnetic radiation source five times for a total of twenty-five flashes per cartridge. It is envisioned that some embodiments may be configured to perform the necessary surface treatment with as little as one single flash, or any integer number of flashes between two and twenty-five, inclusive. Some embodiments can use continuous transport with appropriately timed flashing of the electromagnetic radiation sources 50 and 51.

In some embodiments, a continuous wave of electromagnetic radiation is emitted, for example, from a fog ultraviolet source available from Fogg Filler Company™, Holland Mich. For example, a fog ultraviolet source can have wavelengths between 180 inn and 240 nm. In some embodiments, an optical system can be used to focus the electromagnetic radiation. In some embodiments, a fog electromagnetic radiation source having a continuous electromagnetic radiation with varying wavelengths within the continuous exposure can be used. Alternately, the electromagnetic radiation source can supply electromagnetic radiation of varying wavelengths, varying power density, or varying duration of exposure. For example, the pulsed electromagnetic radiation could be produced in a sinusoidal wave formation or in a square wave formation.

In some embodiments, prior to exposing the surface to the electromagnetic radiation, a surfactant such as an ethanol treatment may be applied to the cartridge. Ethanol may be applied to the surface for treatment to disperse the microbes, which may be in a stacked configuration, prior to exposure to electromagnetic radiation. Ethanol dries faster than water thereby inhibiting a microbe's tendency to form a stacked configuration.

Figure 3:
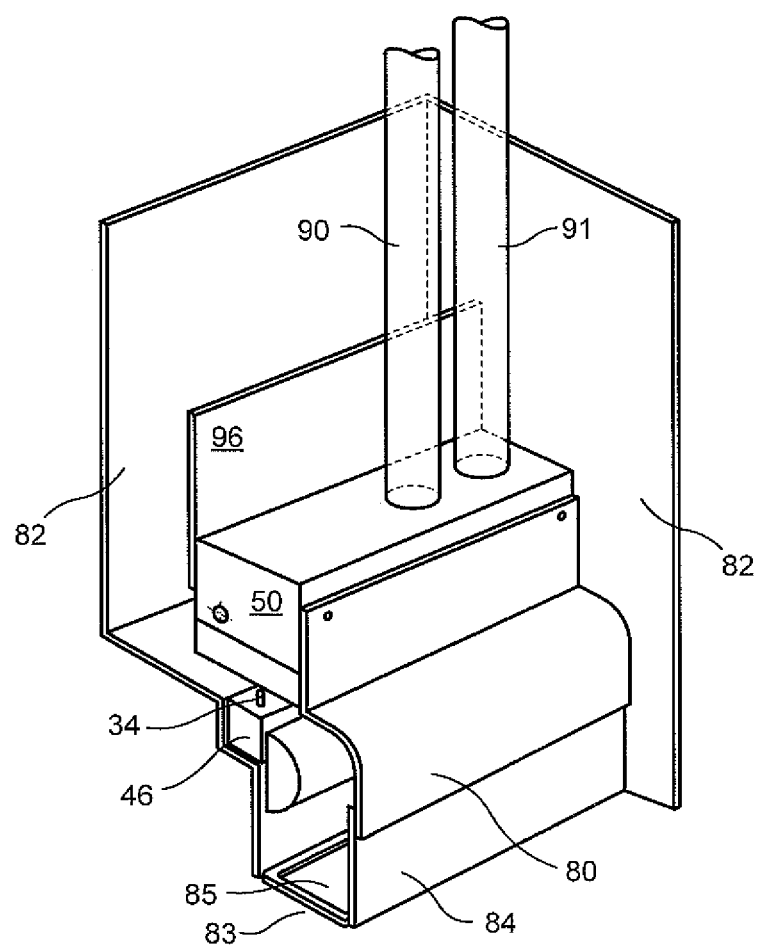
FIG. 3 depicts a front perspective view of an exemplary shielded electromagnetic radiation source and a cartridge that can be used in the system for treating non-sterilized surfaces.

FIG. 3 depicts a side perspective view of an exemplary shielded electromagnetic radiation source that can be used in the system for treating one or more non-sterilized surfaces. As shown in FIG. 3, in order to protect the operator from exposure, the electromagnetic radiation from the electromagnetic radiation source 50 can be shielded by side shields 82. Curved shield 80 extends downwardly from the electromagnetic source 50 and further provides laminar flow direction capabilities. Lower shield 84 extends downwardly from curved shield 80. Lower shield support 83 maintains lower shield 84 in place and provides a central passageway 85 through which the laminar airflow can pass after passing the fixture 46 and being directed downwardly by curved shield 80. Conduits 90, 91 provide a pathway for the ingress and egress of cooling air for the electromagnetic radiation source 50.

FIG. 4 depicts a cross-sectional view of an exemplary source of electromagnetic radiation, a medical device and a shield that can be used in the system for treating non-sterilized surfaces. For illustrative purposes, one side shield 82 is removed from the depiction in order to view the structural arrangement of the source of electromagnetic radiation, the device undergoing treatment and the operator shielding. As shown in FIG. 4, the electromagnetic radiation source 50 is mounted on a hinged assembly 92 and is attached to conduits 90, 91 which provide a pathway for cooling air. The fixture 46, including cartridges 34 (or other surfaces to be sterilized), passes under the electromagnetic radiation source 50. The chamber can further include a curved laminar airflow guide 94 and a straight laminar airflow shield 96 to maintain the laminar airflow and direct it toward the cartridges 34 or other surface to be sterilized. As will be described with respect to FIG. 5, laminar airflow source 100 provides a laminar airflow.

In an exemplary embodiment, the fixture 46 can transport the cartridge 34 through the chamber on a conveyor, a rail, a turntable, a flexible web or a strip. The electromagnetic radiation source 50 can emit an electromagnetic of an appropriate frequency and intensity thereby reducing the contamination level on cartridge 34 or other surface for treatment.

Figure 5:
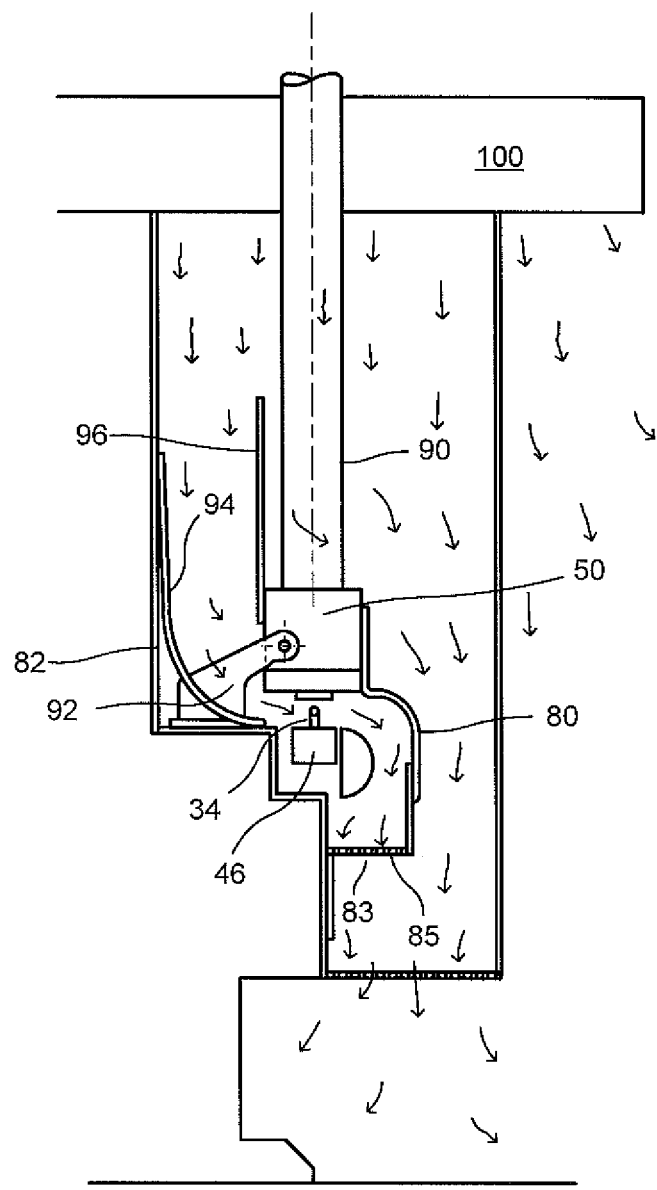
FIG. 5 depicts a cross-sectional view of an exemplary source of electromagnetic radiation and a laminar airflow that can be used in the system for treating non-sterilized surfaces.

FIG. 5 depicts a cross-sectional view of an exemplary source of electromagnetic radiation, a laminar airflow and a medical device that can be used in the system for treating non-sterilized surfaces. As shown in FIG. 5, the laminar airflow source 100 (with the generally downwardly pointing arrows of FIG. 5 indicating the laminar airflow produced thereby) can be configured to be positioned in a vertical plane parallel to the treatment surface. The laminar airflow can be directed toward the fixture 46 between the curved laminar airflow guide 94 and the straight laminar airflow guide 96 and subsequently redirected downwardly by curved guide 80 to ensure a constant stream of airflow (as well as minimizing turbulence which would degrade the laminar character of the airflow) over the fixture 46, including cartridges 34 or other surfaces for treatment.

In some embodiments, the laminar airflow as produced by laminar airflow source 100 can be ISO class 5 airflow. The airflow humidity, volume, pressure, temperature and speed of flow can be configured based on the processing conditions in part that can be determined by the electromagnetic radiation source time and intensity profiles, the total processing time and the rate that the fixtures move through the processing chamber. The process can further utilize the laminar airflow to provide cooling properties to the surface for treatment.

In some embodiments, the laminar airflow may be applied throughout the entire process. The airflow can begin when the cartridge assemblies are loaded onto the fixture and can continue throughout the subsequent process steps through the final step of removing the assembly from the process. In some embodiments, the laminar airflow may be applied incrementally throughout the process or can be applied to specific assembly stations including, but not limited to, a needle assembly station or a sleeve assembly station or the process control station. The laminar airflow may have a consistent flow parameters or variable flow parameters throughout the process.

Figure 6:
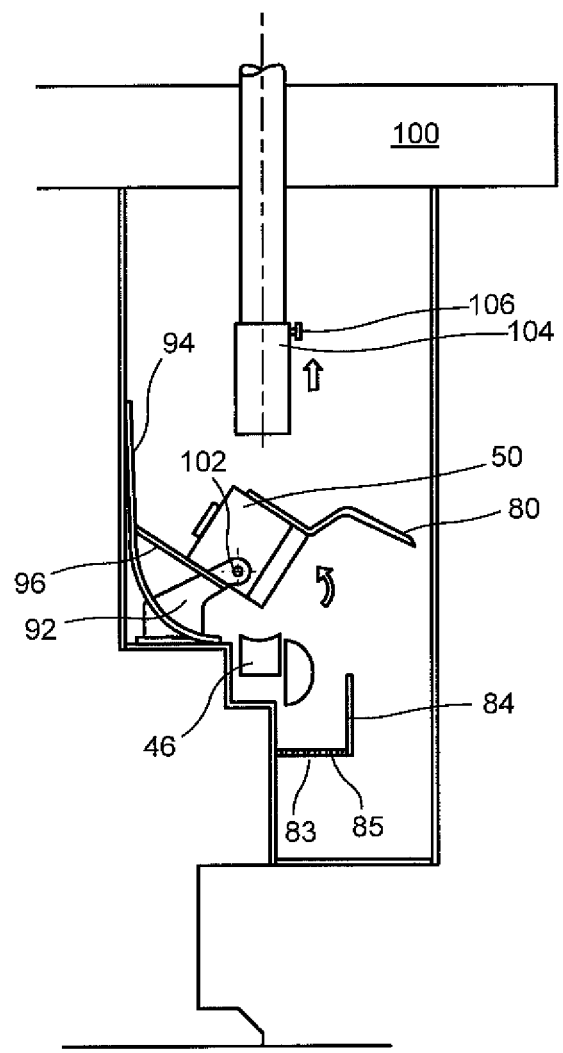
FIG. 6 depicts a cross-sectional view of an exemplary source of electromagnetic radiation in a repair configuration that can be used in the system for treating non-sterilized surfaces.

FIG. 6 depicts a cross-sectional view of a repair/replacement configuration of an exemplary source of electromagnetic radiation that can be used in the system for treating non-sterilized surfaces. As shown in FIG. 6, the hinged assembly 92 can include a hinge member 102 in order to pivot electromagnetic radiation source 50, such as may be done to replace a bulb or other active element. The conduits 90, 91 can be retracted from the electromagnetic radiation source by a sleeve 104 held in position by tightener 106. In an exemplary embodiment, the hinged fixture assembly 92 can pivot around the hinged member 102 rotating the surface of the fixture 46 from a parallel orientation with respect to the electromagnetic radiation source 50 an angled orientation approximately 45 degrees from the original position. Rotation of the fixture 46 can also elevate the curved shield 80. Rotation of the curved shield 80 can enable access to the electromagnetic radiation source 50 for cleaning, repairs and monitoring.

In some embodiments, the electromagnetic radiation can be periodically or continuously monitored using a monitoring system such as LiteMark™ produced by Xenon™ Corporation or a similar device. If a process deviates from the prescribed method of operation, the monitoring system can trigger the machine to stop operations. Control of the process can include monitoring the electromagnetic radiation intensities, returning the relative light intensities for tracking the radiant energy level and process times. Exceeding the process limits or failing to reach the minimum process limits can result in rejected products.

Figure 7:
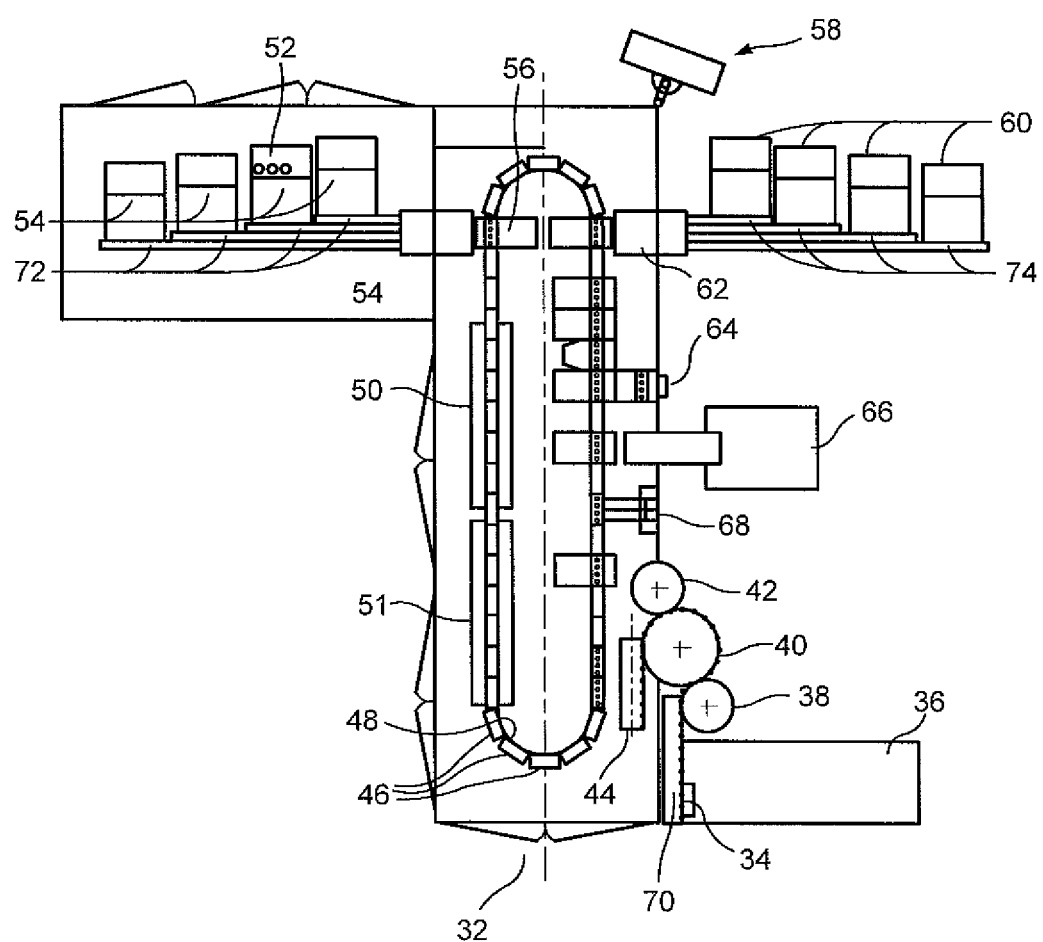
FIG. 7 depicts a top view of an exemplary system for treating non-sterilized surfaces.

FIG. 7 depicts a top view of an exemplary system 32 for treating non-sterilized surfaces. The system 32 can include a cartridge input 36, a fixture 46, a conveyer 48, first and second electromagnetic radiation sources 50, 51, a needle assembly input 52, a sleeve input 60, a process control station 64, an output feeder 66 and a rejected products output feeder 68. The cartridge input 36 can further include a cartridge 34, a cartridge input conveyer 70, a cartridge input turntable 38, a cartridge screening turntable 40, and a cartridge reject turntable 42. The conveyer 48 can further include an in-feeder conveyer 44. The needle assembly input 52 can include a needle assembly 54, an input feeder 72, and a needle assembly station 56. The sleeve input 60 can include a sleeve assembly 62, and an input feeder 74. The system of FIG. 7 further includes the laminar airflow source 100 of FIGS. 4-6.

As shown in FIG. 7, the cartridge input 36 can transfer the cartridge 34 into the cartridge input conveyer 70. The cartridge input conveyer 70, can transfer the cartridge 34 to input turntable 38. Input turntable 38 can rotate in a desired direction. As the cartridge 34 rotates about the central axis of input turntable 38, the cartridge 34 can be transferred to the cartridge screening turntable 40 that can be rotating in an opposite direction. The cartridge 34 can be screened for defective product features that can include physical, mechanical or chemical anomalies. As the cartridge 34 rotates farther about the central axis of cartridge screening turntable 40, defective products can be transferred to the rejected cartridge turntable 42 that can rotate in a desired direction.

The cartridge 34 can then be transferred from the cartridge screening turntable 40 to the in-feeder conveyer 44. From the in-feeder conveyer 44, the cartridge 34 can be loaded into the fixture 46 on the conveyer belt 48. The conveyer belt can include a belt, a rail, rollers, a take-up reel, a feed reel, or the like. In an exemplary embodiment, the fixture 46 can be configured to hold four cartridges 34 per fixture. In an alternate embodiment, the fixture may hold more than four cartridges. For example, five, six, seven, eight, nine, ten, eleven, twelve or more cartridges may be held. The fixture 46 can be configured to hold the cartridges 34 in a single linear row or in multiple rows either in a linear or in a staggered fashion. The conveyer belt or similar device 48 can move the cartridge 34 about an oval path, a circular path or a zig-zag path in a clockwise or counter-clockwise direction.

The conveyer 48 can move the fixture 46 holding the cartridges 34 under the first and second electromagnetic radiation sources 50 and 51. The electromagnetic radiation sources 50 and 51 can emit ultraviolet radiation. In some embodiments, the ultraviolet radiation can be delivered in a pulsed interval to treat the non-sterile surface. In some embodiments, the ultraviolet radiation can be delivered via an electromagnetic radiation source available from Xenon™ Corporation. The conveyor 48 can be configured to move two and a half fixtures 46 or twenty cartridges 34 through the electromagnetic radiation exposure per cycle. The flash frequency can be two seconds, wherein each index is 1.6 seconds exposure then 0.4 seconds without exposure. Each cartridge 34 can be exposed to electromagnetic energy five times for a maximum exposure of twenty-five times per cartridge 34. However, it is envisioned that other embodiments may use more flashes, fewer flashes, or may even achieve the desired objectives with a single flash, or any integer number of flashes between one and twenty-five, inclusive.

Still referring to FIG. 7, one sees that the conveyer 48 can transport the fixture 46 to the needle assembly station 56. The needle assemblies 52 can be loaded onto needle assembly input 54. In some embodiments, the needle assembly input 54 can be a tray, a fixture, or the like. The needle assembly 52 can be pre-sterilized and can be coupled to the cartridge 34 at the needle assembly station 56. In some embodiments, a hopper or the like can hold a supply of sterile needle assemblies and deliver them to a chute. For example, the needle assembly can be deployed by a chute that delivers a sterile needle hub to a position vertically aligned with one of the passing cartridges. A press can receive the needle and press the needle hub on the aligned cartridge at the end of the chute. The anvil can be pressed downward onto the cartridge enabling a receiver to engage a septum without pushing the needle through the septum. In some embodiments, the needle assembly process can be manual. Alternately, the assembly process may be automated.

The conveyer 48 can move the fixture to the sleeve assembly 62. The sleeves 60 can be loaded onto an input feeder 74 and transferred to the sleeve assembly 62. The sleeves 60 can be coupled to the cartridge assembly 34 and the needle assembly 52 contained in the fixture 46. The sleeve can be coupled to the cartridge assembly with a manual or an automatic process. The conveyor 48 can transport the fixture 46 to the process control station 64. In some embodiments, the process control station can evaluate the physical, mechanical or chemical configuration of the device. The conveyor 48 can move the fixture 46 to the output feeder 66. The output feeder 66 can remove the devices from the fixture 46 and the conveyer 48. The conveyer 48 can then move the cartridges 34 that have failed the process control inspection to the output feeder to remove rejected products 68. The fixture 46 can then move back to the turntable 40 to be reloaded and the process can be restarted.

Figure 8A:
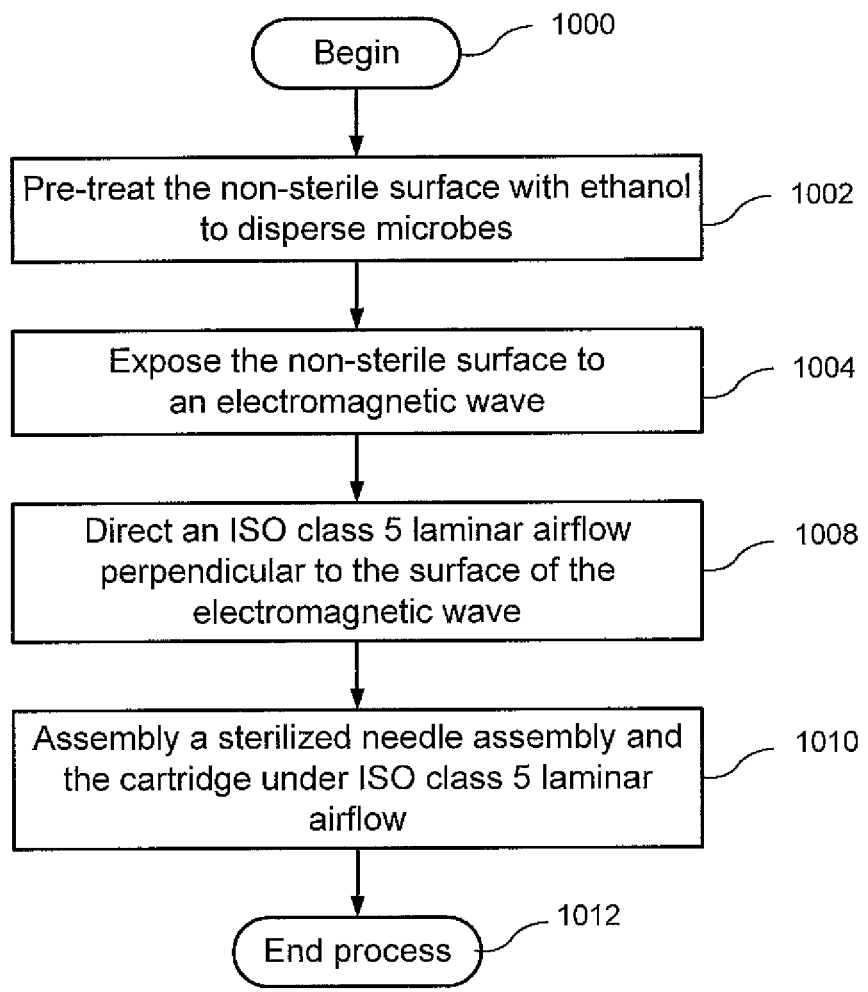
FIG. 8A is a flow diagram that illustrates a method of treating a non-sterilized surface in accordance with exemplary embodiments of the present disclosure.
Figure 8C:
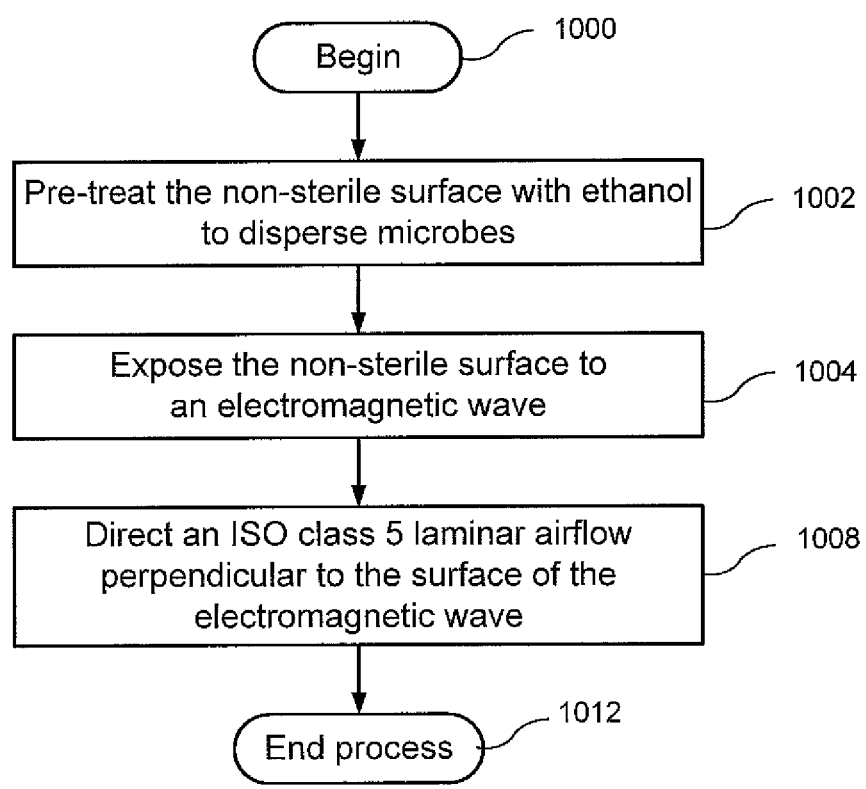
FIG. 8C is a flow diagram that illustrates a third method of treating a non-sterilized surface in accordance with exemplary embodiments of the present disclosure.

FIGS. 8A, 8B and 8C are flow diagrams that illustrates a method of treating a non-sterilized surface in accordance with exemplary embodiments of the present disclosure. For example, the method of treating a non-sterilized surface may include an electromagnetic radiation source, a laminar airflow and a surface to be treated to result in a logarithmic reduction of contaminants on the surface, such as, but not limited to, a septum of a cartridge held within a fixture.

As shown in FIG. 8A, at step 1000, the method of treatment for the non-sterilized surface may begin. At step 1002, the non-sterile surface can optionally be pre-treated with ethanol to disperse microbes. At step 1004, the non-sterile surface of a cartridge can be exposed to an electromagnetic wave. The cartridge can include a septum or diaphragms used to manufacture 1.7 mL cartridges containing injectable agents. The electromagnetic wave can have a pulsed light intensity in the form of a square wave. At step 1008, a direct ISO class 5 laminar airflow can be directed perpendicularly to the surface of the cartridge simultaneously exposing the surface for treatment to the electromagnetic wave and the laminar airflow. The laminar airflow can keep the surface for treatment free of contaminants to ensure that a fluid pathway of the device remains free of contaminants. At step 1010, the pre-sterilized needle assembly and the cartridge can optionally be assembled under an ISO class 5 laminar airflow. At step 1012, the process ends with a surface with an acceptable sterility assurance level (SAL), and, in some embodiments, may include an assembled pre-sterilized needle assembly and a cartridge.

FIG. 8B illustrates that step 1002, the use of ethanol to disperse microbes, is optional and may be omitted. Similarly, FIG. 8C illustrates that the assembly step of 1010 is optional and may be omitted or varied, particularly in view of treatment of different surfaces.

Figure 9:
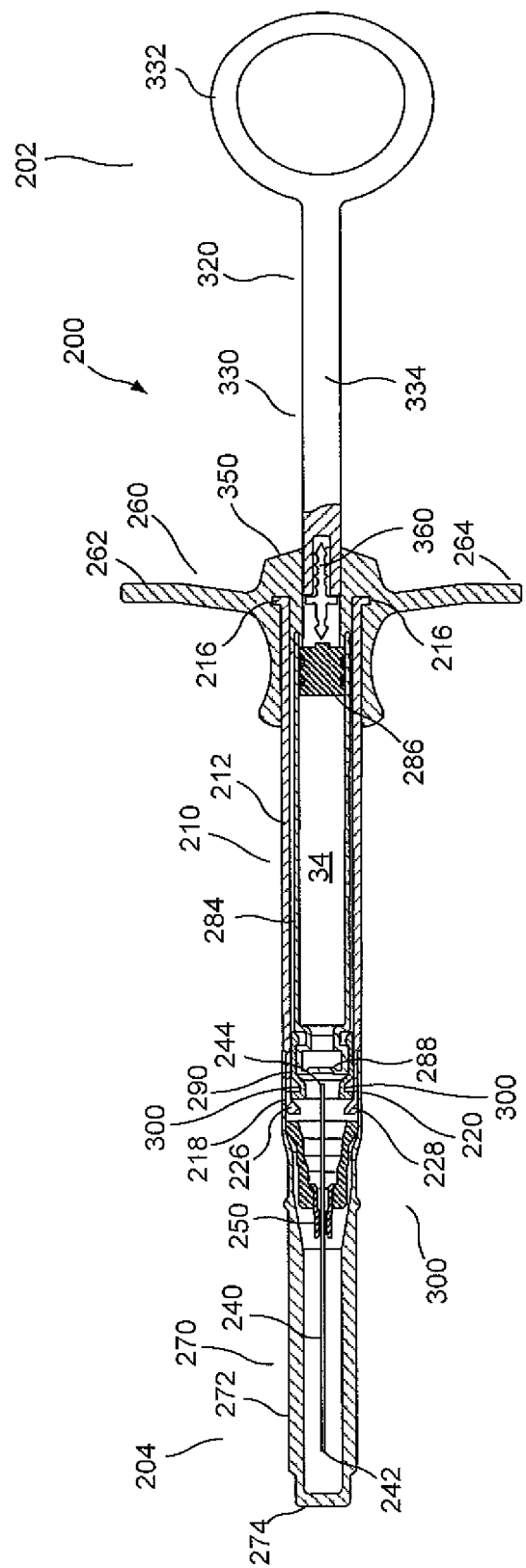
FIG. 9 is a cross-sectional view of a first assembled injection device of the present disclosure in the pre-armed configuration.

FIG. 9 is a cross-sectional view of one exemplary injection device 200 which may be assembled using a cartridge 34 sterilized by the system and method of the present disclosure, for example, the systems depicted in any of FIGS. 1A, 1B, and 2-7. The injection device 200 is a single-patient, single-use, disposable, sterile injection device pre-loaded with an injectable agent. As shown in FIG. 9, the fully assembled injection device 200 can have a proximal end 202 and a distal end 204, in a pre-armed state (i.e., a sterility barrier of the cartridge 34 has not been pierced by the butt end 244 of the needle cannula 240 prior to the formation of a continuous sterile pathway from the cartridge 34 to the tip 242 of needle cannula 240 to inject the injectable agent), with a cartridge 34 concentrically surrounded by housing 210. The cartridge 34 includes a cartridge plunger 286 on one end and a cap or band 288 on the other end that secures a septum 289 thereto. The septum 289 forms one sterility barrier to maintain sterility of a liquid held in the cartridge 34. A cartridge-to-housing interface 290 engages the cap 288 of the cartridge 34. The housing 210 includes first and second cantilevered locking tabs 218, 220, which are constrained from outward flexure by the outward concentric engagement of the needle sheath 270. Needle sheath 270 includes a generally cylindrical, wall 272 with a closed end 274. The sheath 270 is formed from polyethylene or polypropylene, but is not limited thereto. The cantilevered first and second locking tabs 218, 220, in this constrained position, prevent the forward movement of the cartridge-to-housing interface 290 and the cartridge 34 thereby maintaining a separation between the butt end 244 of the cannula 240 and the septum 289 of cartridge 34 held in place by cap or band 288. The cannula crimp insert 250, can be made from stainless steel or a similar material, but not limited thereto.

In the armed state (i.e., piercing of the sterility barrier by the butt end 244 of the needle cannula 240 to form a continuous sterile pathway from the cartridge 34 to the tip 242 of cannula 240 to inject the injectable agent) of injection device 200, the needle sheath 270 can be removed thereby allowing outward flexure of the first and second locking tabs 218, 220 and further allowing the cartridge 34 and cartridge-to-housing interface 290 to be moved forward toward the distal end 204 by motion on the plunger rod 330 so that the butt end 244 of the cannula 240 penetrates the septum 289 of the cartridge 34. As the cartridge 34 and cartridge-to-housing interface 290 are moved forward relative to the fixed housing 210, first and second latching bosses 226, 228 engage the annular notch 300 of the cartridge-to-housing interface 290. In this armed state, the injection device 200 is ready for use by a medical professional. It should be noted that while the first and second latching bosses 226, 228 are illustrated as being inwardly extending, that it is envisioned that this disclosure, particularly regarding latching and engagement elements, could encompass many different equivalent structures, for example, detents, stops, latches, catches and the like.

As shown in FIG. 9, the plunger rod assembly 320 which includes plunger rod 330, plunger cap 350 and harpoon 360. The plunger rod 330 and plunger cap 350 are made from hard polyethylene or polypropylene, but are no limited thereto while the harpoon 360 is made from stainless steel or a similar material, but is not limited thereto. Plunger rod 330 includes circular thumb ring 332 and shaft 334.

As shown in FIG. 9, the finger flange assembly 260 is formed from injection molded plastic, but is not limited thereto, and may have no sterility requirement. Finger flange assembly 260 has two finger flanges 262, 264 for use by the medical practitioner during injection and further has a rear annular rim 216 of housing 210. The housing 210 can include a cylindrical body 212 having a cylindrical wall 284. Rotatable engagement between the finger flange assembly 260 and the housing 210 allows the user or medical practitioner to orient the bevel 242 of the needle cannula 240 during use. Bevel orientation can be achieved in other ways, such as, but not limited to, a fixed finger flange assembly in combination with either a rotating plunger rod or a plunger rod with a rotating harpoon.

FIGS. 10 and 11 illustrate the axial relationship and configuration of the cartridge 34 and the cartridge-to-housing interface 290. The cartridge 34 can include cylindrical glass wall 284, containing the injectable agent therein, and further includes a cartridge plunger 286 at one end and an aluminum cap or band 288 at the other end, holding a septum 289 in place.

The cartridge-to-housing interface 290 is formed from hard polyethylene or polypropylene, but is not limited thereto, and includes a first end 292 with cylindrical wall 294 for forming a tight fit around the cap 288 of cartridge 34, holding septum 289 in place. As shown in FIGS. 12A and 12B, the cap 288 holds the septum 289 in place (FIG. 12A discloses a single layer septum 289 while FIG. 12B discloses a dual layer septum 289), exposed through opening 291 in cap 288. The combination of the cap 288 and the septum 289 form a piercable sterility barrier to maintain sterility of the contents of the pre-loaded cartridge 282. Cartridge-to-housing interface 290 further includes a central passageway 296 for communication between the first end 292 and second end 298. Second end 298 includes outwardly flared edge 299. Immediately inwardly adjacent from second end 298, annular notch 300 is formed.

As shown in FIGS. 10 and 11, the cartridge-to-housing interface 290 (which has been sterilized by gamma ray, ultraviolet or a similar method as appropriate to the design) and cartridge 34 are brought into a controlled area (laminar airflow ISO class air supply). During surface treatment to result in an acceptable sterility assurance level (SAL), the cartridges 34 are oriented vertically with the cap 288 on top and have their top surface treated with pulsed or continuous ultraviolet light, such as is taught in the present disclosure for example, the systems depicted in any of FIGS. 1A, 1B, and 2-7. The cartridge-to-housing interface 290 is then pressed onto the cap 288 as shown in FIGS. 10 and 11 whereby the interior of cylindrical wall 294 of the first end 292 of the cartridge-to-housing interface 290 forms a friction fit with the cap 288 of cartridge 34 thereby forming second sterile barrier, extending circumferentially around the cap 288 of the cartridge-to-housing interface 290 providing a maximum insertion, and a seat for the cartridge 34 while the cartridge-to-housing interface 290 snap engages the cap 288 of cartridge 34. This results in a subassembly 318 which can be used for subsequent assembly of a single-use injection device of FIG. 9. It should be noted that the cap 288 and surrounding areas of the cartridge 34 achieve the acceptable sterility level (SAL) by exposure to the electromagnetic radiation sources 50, 51, while remaining areas of the surface of the cartridge 34 may remain contaminated.

Figure 13:
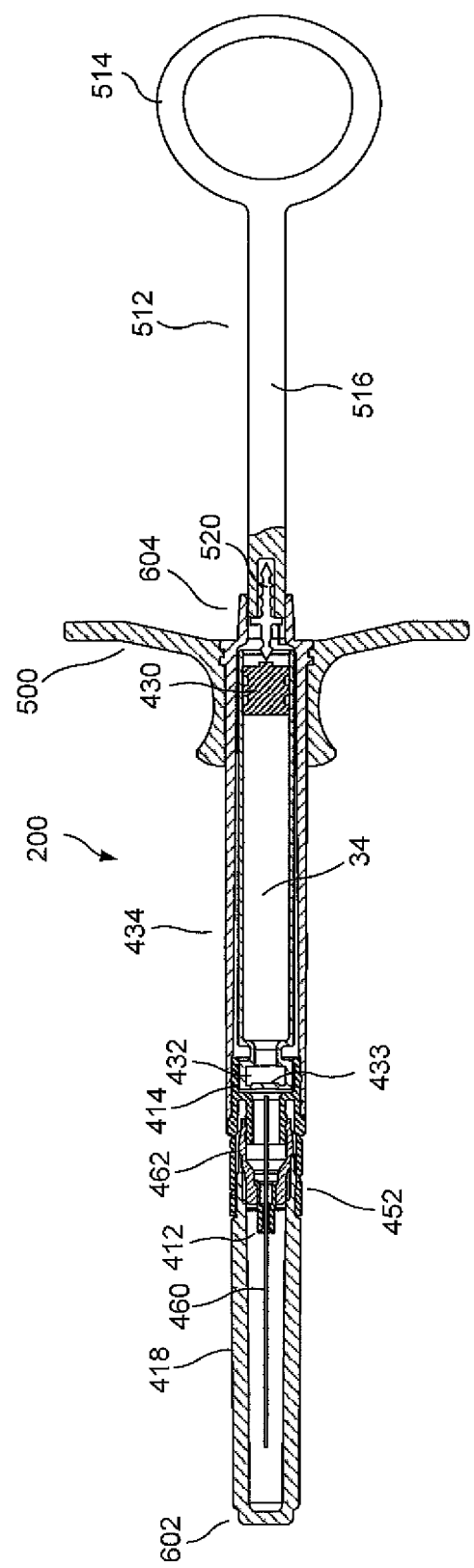
FIG. 13 is a cross-sectional view of a second assembled injection device of the present disclosure in the pre-armed configuration.

FIG. 13 is a cross-sectional view of another exemplary injection device 200 which may be assembled using a cartridge 34 sterilized by the system and method of the present disclosure, for example, the systems depicted in any of FIGS. 1A, 1B, and 2-7. FIG. 13 illustrates the pre-armed state, with a cartridge 34 concentrically surrounded by housing 434. The cartridge 34 includes a cartridge plunger 430 on one end and a cap or band 432 that secures a piercable septum 33 thereto on the other end. The piercable septum 33 forms one sterility barrier to maintain sterility of the injectable agent held in the cartridge 34. A hub-to-cartridge interface 414 engages the cap 432 of the cartridge 34 as well as providing for two mounting positions for the hub 462 of needle assembly 412. In the first mounting position, which is illustrated in FIG. 13, the injection device 200 is in its pre-armed state. The interaction and interface of the needle sheath 418 with the peel tab 452 forms another sterility barrier to maintain the sterility of the cannula 460 during packing, shipping and storage until the peel tab 452 is disengaged by the medical professional.

Finger flange assembly 500 is mounted on the housing 434 at the proximal end 604 of the injection device 200. In some embodiments, the finger flange assembly 500 is rotatable about the housing 434. The plunger rod assembly 512 includes a thumb ring 514 and a shaft 516 which further includes a harpoon 520 which engages the cartridge plunger 430 of the cartridge 34.

FIGS. 14A and 14B, depict the insertion and axial relationship of the cartridge 34 and the hub-to-cartridge interface 414. Cartridge 34 which may be a drug carpule, includes glass cylindrical walls 486 forming a storage volume for an injectable agent. The cartridge 34 includes a cartridge plunger 430 at one end and a cap 432 at the other end. The needle assembly 412 (which has been sterilized by gamma ray, ultra-violet or a similar method) and cartridge 34 are brought into a controlled area (laminar airflow ISO class air supply). The cartridge 34 is oriented vertically with the cap 432, for example, an aluminum band or cap, on top and its top surface is treated with pulsed or continuous ultraviolet light, such as is taught in the present disclosure for example, the systems depicted in any of FIGS. 1A, 1B, and 2-7. The needle assembly 412 is then pressed onto the cap 432 as shown in FIG. 14B, whereby the interior of the hub-to-cartridge interface 414 forms a friction fit with the cap 432 of cartridge 34. Additionally, the hub-to-cartridge interface 414 maintains a sterile barrier around the cap 432 and holds the assembly in position.

Example System and Method

An example system has been designed and constructed. The example system uses an electromagnetic radiation source having a PCN controller with an external controller-timer, a LH 840 lamp housing with 890-1957, type C flash-lamp and a PS-812/815 power supply. Bacillus atrophaeus spores (e.g., $1.13 \times 10^6$ per 0.1 mL in 40% ethanol solution, product reference SUS-1-6, Mesa Labs, lot SSG372) were selected as the organisms for the studies. They are a preferred organism for sterilization validation studies and available as suspensions in various concentrations. Septums (diaphragms) used to manufacture cartridges containing injectable agents were obtained from Septodont-Novocol Pharmaceutical of Canada. The septums were sized to manufacture 1.7 mL cartridges. Prior to use, the Septodont drug cartridge septums were autoclave sterilized in steam permeable pouches. Test septums were inoculated with targeted quantities of Bacillus atrophaeus spores by pipetting calculated quantities of enumerated Bacillus atrophaeus spores suspension onto the center of the septum and allowing the inoculum to dry in a laminar flow microbiology cabinet. Negative Control septums (N=2, no inoculum) and a Positive Control septums (N=2, $10^4$ inoculum) were prepared for each study.

The alignment of the septums under the electromagnetic radiation source was verified using New UV Intensity Labels, part number N010-005, from UV Process Supply, Inc. Polytetrafluoroethylene and aluminum septums were autoclave sterilized and then used to present the inoculated septums into the electromagnetic radiation source apparatus. Inoculated test septums were then exposed to electromagnetic radiation source as required in the study procedures.

Example Results for Log Reduction Quantitative Study (Study #1)

Sterile septums were inoculated with an estimated $5.65 \times 10^4$ Bacillus atrophaeus spores. Five inoculated specimens were treated by electromagnetic radiation source exposure at each of the following test condition; four groups of electromagnetic radiation source exposures consisting of five specimens per group. The groups were exposed to two electromagnetic radiation source pulse exposures, three electromagnetic radiation source pulse exposures, four electromagnetic radiation source pulse exposures, or eight electromagnetic radiation source pulse exposures. The surviving organisms were recovered by extraction from the septums into 10-mL of sterile saline. Viable organisms were enumerated by plating the saline onto two trypic soy agar plates and incubated at 30°-35° C. The number of colonies indicating the number of viable organisms was counted. Log reduction resulting from the electromagnetic radiation source exposure was calculated.

The results of the Log Reduction Quantitative Study indicate that there is a reduction in population of viable Bacillus atrophaeus spores on the drug cartridge septum due to electromagnetic radiation source exposure. The reduction in viable spore population decreased with increasing quantities of electromagnetic radiation source pulse exposures. The full potential for logarithmic reduction of bacterial spores with the electromagnetic radiation source pulse exposures is probably underestimated in the reported study because the number of viable spores approached zero for the study conditions of three, four and eight pulse exposures.

The study may underestimate the log reduction power of the electromagnetic radiation source exposures because the mathematics of the calculation requires that the number of viable colonies be counted as N=1 even if no colonies indicating surviving organisms were observed. Although the level of population reduction (kill) appears to be related to the number of electromagnetic radiation source pulses, the limitations of the log reduction calculation method make the exact expose-log reduction relationship difficult to predict. The Study 1 results are summarized in Table 1.

TABLE 1

Results for Log Reduction Study 1

| Exposure - Number UV Pulses | Log of Initial Inoculum Population | Log of Surviving Inoculum Population[1] | Log Reduction[1] |
| --- | --- | --- | --- |
| 2 | 4.75 | 2.19 | 2.56 |
| 3 | 4.75 | 1.42 | 3.33 |
| 4 | 4.75 | 1.23 | 3.47 |
| 8 | 4.75 | 1.24 | 3.51 |

[1]Average of five samples

Example Results for Further Log Reduction Quantitative Study (Study #2)

The sterile septums were inoculated with an estimated $2.4 \times 10^8$ Bacillus atrophaeus spores. Five inoculated specimens were treated by electromagnetic radiation source exposure at each of the following test condition; four groups of electromagnetic radiation source exposures consisting of five specimens per group. The groups were exposed to four, eight, twelve, sixteen or twenty-four electromagnetic radiation source pulse exposures. The surviving organisms were recovered by extraction from the septums into sterile saline. Viable organisms were enumerated by dilution and plating the saline onto two trypic soy agar plates and incubated at 30°-35° C. The number of colonies indicating the number of viable organisms was counted. Logarithmic reduction resulting from the electromagnetic radiation source exposure was calculated.

The results of the Log Reduction Quantitative Study indicate that there is a reduction in population of viable

*Bacillus atrophaeus* spores on the drug cartridge septum due to electromagnetic radiation source exposure. The calculated maximum logarithmic reduction in viable spore population in Study #2 was greater than in Study #1 because of the higher starting spore population used in the study. The Study #1 results are summarized in Table 2. It should be noted that, in some tests, higher levels of organisms may result in a higher degree of layering of organisms, thereby resulting in some tests results with a lower reduction of organisms, notwithstanding a same or higher number of pulses of electromagnetic energy, as compared to other tests. As understood by the inventors, the increase in the number of organisms in the target area also increases the occurrence of layering of organisms in the target area. Consequently, the bodies of organisms forming the top layer(s) shield the organisms at lower layers requiring greater total exposure to achieve the killing of the organism to reach an acceptable SAL.

TABLE 2

Results for Log Reduction Study 2

| Exposure - Number UV Pulses | Log of Initial Inoculum Population | Average Log of Surviving Inoculum Population[1] | Average Log Reduction[1] |
|---|---|---|---|
| 4 | 8.1 | 6.9 | 1.2 |
| 8 | 8.1 | 6.5 | 1.6 |
| 12 | 8.1 | 6.4 | 1.7 |
| 16 | 8.1 | 5.5 | 2.6 |
| 24 | 8.1 | 1.7 | 6.3 |

[1]Average of five samples

Sterile septums were inoculated with an estimated $2.3 \times 10^4$ *Bacillus atrophaeus* spores. Inoculated specimens were treated by electromagnetic radiation source light exposure as indicated by the Table 3 below. Treated septums were dropped into test tubes containing 15 mL trypic soy broth and incubated at 30°-35° C. The test tubes were inspected periodically through fourteen days for indication of bacterial growth which would indicate that the *Bacillus atrophaeus* spores remained viable after the exposure conditions.

TABLE 3

Results for Spore Recovery Efficacy Studies

| | Number of ultraviolet pulse exposures for TEST Septums | | | | | | | | | |
|---|---|---|---|---|---|---|---|---|---|---|
| | 4 | 6 | 7 | 8 | 9 | 10 | 11 | 17 | 20 | 24 |
| Study 2 Number of specimens | 10 | 10 | — | — | 10 | 10 | 10 | 10 | 10 | 10 |
| Study 3 Number of specimens | — | 10 | 10 | 20 | 10 | 20 | — | — | — | — |

The results from spore recovery Studies 2 and 3 are tabulated in Table 4 and show a clear relationship between the number of electromagnetic radiation source pulse exposures and the number of inoculated septums on which all of the *Bacillus atrophaeus* spores were killed. Only 1 of 10 of samples inoculated with $2.3 \times 10^4$ *Bacillus atrophaeus* were free of viable *Bacillus atrophaeus* spores after 4-pulses. The number of septums with surviving spores decreased as the electromagnetic radiation source exposure was increased. All samples were free of viable *Bacillus atrophaeus* spores and therefore considered to be sterile at exposures of ≥10 pulses.

TABLE 4

Results for Quantitative Studies 2 and 3: Number of Sterile Specimens (Negative for Microbial Growth) at 14 Days (number sterile/number tested)

| Exposure - Number UV Pulses | Study 2 | Study 3 | Combined Results |
|---|---|---|---|
| 4 | 1/10 | — | 1/10 = 10% |
| 6 | 6/10 | 3/10 | 9/20 = 45% |
| 7 | — | 4/10 | 4/10 = 40% |
| 8 | — | 15/20 | 15/20 = 75% |
| 9 | 10/10 | 7/10 | 17/20 = 80% |
| 10 | 10/10 | 20/20 | 30/30 = 100% |
| 11 | 10/10 | — | 10/10 = 100% |
| 17 | 10/10 | — | 10/10 = 100% |
| 20 | 10/10 | — | 10/10 = 100% |
| 24 | 10/10 | — | 10/10 = 100% |
| Negative Controls | 0/2 | 0/2 | |
| Positive Controls | 2/2 | 2/2 | |

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made expressed herein, without departing from the spirit and scope of the invention.

The invention claimed is:

1. A system for treating a non-sterile first surface of a cartridge pre-filled with an injectable agent, the system comprising:
   a pre-filled cartridge filled with an injectable agent including one of local anesthetics, therapeutic or pharmaceutical agents, cosmetic agents or liquids, gels or powders in the medical, dental, veterinary or cosmetic fields;
   a source of electromagnetic radiation emitting electromagnetic radiation on a non-sterile first surface of the prefilled cartridge, wherein exposure of the non-sterile first surface of the prefilled cartridge to the emitted electromagnetic radiation results in a logarithmic reduction of contamination on the non-sterile first surface; and
   a fixture for holding the pre-filled cartridge, the fixture being located in a path of the emitted electromagnetic radiation from the source of electromagnetic radiation, the fixture comprising a cavity sized and shaped to surround the pre-filled cartridge except at the non-sterile first surface to prevent the emitted electromagnetic radiation from entering the cartridge and reduce exposure of the injectable agent;
   a laminar airflow source providing laminar airflow to the non-sterile first surface to simultaneously expose the non-sterile first surface of the prefilled cartridge to the laminar airflow and the electromagnetic radiation emitted by the source of electromagnetic radiation.

2. The system of claim 1, wherein the laminar airflow source is an ISO class 5 laminar airflow source.

3. The system of claim 1 further comprising, a shield at least partially enclosing the source of electromagnetic radiation.

4. The system of claim 1 further comprising, an air flow guide to direct the laminar airflow over the first surface for treatment of the prefilled cartridge, the guide including a first curved wall positioned upstream of the fixture to direct the airflow from the laminar airflow source and a second curved wall positioned downstream of the fixture to direct airflow from the laminar airflow source.

5. The system of claim 1, wherein subsequent to the exposure of the nonsterile first surface to electromagnetic energy and the laminar airflow perpendicular to the nonsterile first surface, the prefilled cartridge includes a fluid pathway free of contamination.

6. The system of claim 1, wherein the electromagnetic radiation is a continuous electromagnetic wave.

7. The system of claim 1, wherein the electromagnetic radiation is ultraviolet radiation.

8. A method for treating a non-sterile first surface of a pre filled cartridge comprising the steps of:
 placing the prefilled cartridge a selected distance from a source of electromagnetic radiation, the prefilled cartridge being filled with an injectable agent including one of local anesthetics, therapeutic or pharmaceutical agents, cosmetic agents or liquids, gels or powders in the medical, dental, veterinary or cosmetic fields; wherein the prefilled cartridge is placed in a fixture for holding the pre-filled cartridge, the fixture being located in a path of the emitted electromagnetic radiation from the source of electromagnetic radiation, the fixture comprising a cavity sized and shaped to surround the pre-filled cartridge except at the non-sterile first surface to prevent the emitted electromagnetic radiation from entering the cartridge and reduce exposure of the injectable agent;
 exposing the non-sterile first surface of the prefilled cartridge to electromagnetic radiation emitted by the source, wherein exposure of the non-sterile first surface of the prefilled cartridge to the emitted electromagnetic radiation results in a logarithmic reduction of contamination on the non-sterile first surface of the prefilled cartridge; and
 directing a laminar airflow perpendicular to the non-sterile first surface of the prefilled cartridge to simultaneously expose the non-sterile first surface of the prefilled cartridge to the laminar airflow and the electromagnetic radiation.

9. The method of claim 8, wherein the electromagnetic radiation is emitted in pulses.

10. The method of claim 8 further comprising, pretreating the non-sterile first surface of the prefilled cartridge with ethanol.

11. The method of claim 8, wherein the selected distance is about 20-30 mm.

12. The method of claim 8, wherein the selected distance is about 25 mm.

13. The method of claim 8, wherein the step of exposing the non-sterile first surface of the prefilled cartridge to electromagnetic energy includes a duration of at least 1.6 seconds.

14. The method of claim 13 wherein the duration of at least 1.6 seconds is followed by an interval of 0.4 seconds free of exposure to electromagnetic energy.

15. The method of claim 8, wherein the fixture receives a plurality of prefilled cartridges such that the respective non-sterile first surfaces of the prefilled cartridges are exposed to the electromagnetic radiation and respective second surfaces of the prefilled cartridges are shielded from the electromagnetic radiation.

16. A cartridge treatment apparatus comprising:
 a fixture for receiving a filled cartridge;
 a source of electromagnetic radiation emitting electromagnetic radiation for treating a nonsterile first surface of a filled cartridge, wherein treatment of the non-sterile first surface by the electromagnetic radiation results in a logarithmic reduction of contamination on the non-sterile first surface of the filled cartridge;
 a source of a laminar airflow, wherein the laminar airflow is directed to the non-sterile first surface of the filled cartridge to expose the non-sterile first surface to the laminar airflow simultaneously with treatment by the source of electromagnetic radiation; and
 an air flow guide to direct the laminar airflow over the first surface for treatment of the filled cartridge in the fixture, the guide including a first curved wall positioned upstream of the fixture to direct the airflow from the laminar airflow source and a second curved wall positioned downstream of the fixture to direct airflow from the laminar airflow source.

17. The cartridge treatment apparatus of claim 16, further including a conveyor for transporting cartridges to the electromagnetic radiation and laminar airflow, the conveyor including the fixture thereby exposing the nonsterile first surface of the filled cartridge to the electromagnetic radiation and shielding a second surface of the cartridge from the electromagnetic radiation.

18. The cartridge treatment apparatus of claim 16 wherein the electromagnetic radiation is pulsed.

19. The cartridge treatment apparatus of claim 16, wherein the source of the electromagnetic radiation is positioned 20 to 30 mm above a top of the filled cartridges.

20. The cartridge treatment apparatus of claim 16, wherein subsequent to the exposure of the non-sterile first surface to electromagnetic energy and the laminar airflow perpendicular to the non-sterile first surface, the filled cartridge includes a fluid pathway free of contamination.

21. The cartridge treatment apparatus of claim 16, wherein the electromagnetic radiation is a continuous electromagnetic wave.

22. The cartridge treatment apparatus of claim 16, wherein the electromagnetic radiation is ultraviolet radiation.

23. The cartridge treatment apparatus of claim 16, wherein the first curved wall is positioned to direct the airflow from the laminar airflow source laterally across the filled cartridge.

* * * * *